US007285696B2

(12) United States Patent
Schmidt et al.

(10) Patent No.: US 7,285,696 B2
(45) Date of Patent: Oct. 23, 2007

(54) PROCESS FOR CATALYTIC ALKYLATION OF MONOCYCLIC AROMATIC COMPOUNDS AND COMPOSITION FOR USE THEREIN

(75) Inventors: Iver Schmidt, Copenhagen (DK); Claus Hviid Christensen, Lynge (DK); Christina Christensen, Lynge (DK); Kim Johannsen, Holte (DK)

(73) Assignee: Haldor Topsoe A/S, Lyngby (DK)

( * ) Notice: Subject to any disclaimer, the term of this patent is extended or adjusted under 35 U.S.C. 154(b) by 134 days.

(21) Appl. No.: 10/840,644

(22) Filed: May 7, 2004

(65) Prior Publication Data

US 2004/0254410 A1   Dec. 16, 2004

(30) Foreign Application Priority Data

May 17, 2003  (DK)  ............... 2003 00746

(51) Int. Cl.
*C07C 2/68* (2006.01)
(52) U.S. Cl. .................................... 585/467
(58) Field of Classification Search ............... 585/467
See application file for complete search history.

(56) References Cited

U.S. PATENT DOCUMENTS

| 3,751,504 A | 8/1973 | Keown et al. |
| 4,016,218 A | 4/1977 | Haag et al. |
| 4,547,605 A | 10/1985 | Kresge et al. |
| 5,118,894 A | 6/1992 | Le |
| 5,118,896 A | 6/1992 | Marker et al. |
| 5,430,211 A * | 7/1995 | Pogue et al. ............. 585/323 |
| 6,002,057 A | 12/1999 | Hendriksen et al. |
| 6,060,632 A | 5/2000 | Takamatsu et al. |
| 2001/0003117 A1 | 6/2001 | Jacobsen et al. |
| 2002/0034471 A1 | 3/2002 | Jacobsen et al. |

FOREIGN PATENT DOCUMENTS

| EP | 0 340 862 | 11/1989 |
| EP | 1 106 575 | 6/2001 |
| WO | WO 98/07673 | 2/1998 |

* cited by examiner

*Primary Examiner*—Thuan Dinh Dang
(74) *Attorney, Agent, or Firm*—Dickstein Shapiro LLP

(57) ABSTRACT

A process for the catalytic alkylation of monocyclic aromatic compounds in a hydrocarbon process stream comprising contacting the monocyclic aromatic compound-containing hydrocarbon process stream with an alkylation agent under alkylation conditions with a mesoporous zeotype catalyst having an intracrystalline, non-crystallographic mesopore system and a mesopore volume of the zeotype crystals above 0.25 ml/g.

11 Claims, No Drawings

PROCESS FOR CATALYTIC ALKYLATION OF MONOCYCLIC AROMATIC COMPOUNDS AND COMPOSITION FOR USE THEREIN

The present invention relates to a process for the production of alkylated monocyclic aromatic compounds by alkylation of monocyclic aromatic compounds with an alkylation agent. In particular, the invention pertains to the catalysation of the alkylation process by a mesoporous zeotype catalyst.

An important process is the production of ethylbenzene, which is a valuable industrial chemical used in the production of styrene monomer for polystyrene. A typical reaction route for obtaining ethylbenzene is the vapour phase alkylation of benzene using ethene as the alkylating agent in the presence of a solid, acidic catalyst. This catalyst usually contains a certain amount of an acidic molecular sieve, typically ZSM-5. Reaction temperatures range from the critical temperature of benzene, 289.5° C. up to approximately 500° C. Reaction pressures vary from atmospheric pressure up to 30 bars typically being in the range 5-20 bars. The molar ratio of benzene to ethene (benzene/ethene ratio) varies from 1:1 to 25:1, a typical value being 5:1. Under favourable process conditions this results in a satisfactory product yield.

Ethylbenzene can be alkylated further to dialkylated products, which results in a decreased selectivity towards the preferred product ethylbenzene. Additionally, diethylbenzenes and ethene oligomerisation compounds are significant coke precursors, which might result in deactivation of the catalyst. Introducing a secondary transalkylation reactor, where diethylbenzene reacts with benzene to form additional ethylbenzene as described in U.S. Pat. No. 3,751,504 can counteract lowering of the product yield.

Alternatively, the diethylbenzenes might be recycled to the alkylation reactor, where the transalkylation between diethylbenzene and benzene can also take place. Furthermore, an excess of benzene, e.g. a molar ratio of benzene/ethene of 5:1 results in increased selectivity to ethylbenzene in the alkylation step. However, this high molar ratio results in a significant excess of benzene, which needs to be recirculated into the alkylation reactor increasing the operational costs of the process. Thus, a high selectivity to ethylbenzene at a low benzene/ethene molar ratio is of key importance. Further details can be found in U.S. Pat. Nos. 4,547,605, 4,016,218 and 5,118,894.

Liquid phase ethylation of benzene is also known using catalysts such as zeolite β as described in U.S. Pat. Nos. 6,060,632 and 6,002,057, and the material known as MCM-41, which is described in U.S. Pat. No. 5,118,894. When using zeolite β a molar ratio of benzene to ethene of 3 can be achieved lowering the amount of benzene re-circulated, and a corresponding increased formation of diethylbenzene is observed. A significantly higher pressure is needed for the process to be economically viable and the ethene streams must be of high purity, i.e. polymer grade ethene. This is in contrast to gas-phase processes, where diluted ethene streams from e.g. a steam cracker or a fluid catalytic cracking unit might be used without upgrading the ethene stream to polymer grade quality.

EP patent No. 922,020 describes a process for preparing an alkylated benzene using a zeolite alkylation or transalkylation catalyst including mesoporous aluminosilicates.

These mesoporous materials have been defined as having pores with a diameter or critical dimension greater than 20 Å up to 200 Å.

Conventional microporous zeotype catalysts have the disadvantage of having a limited surface area available for access of the reactant molecules to the active sites present in the catalyst crystals.

Combining the enhanced transport properties of mesoporous materials with the shape-selectivity and intrinsic catalytic activity associated with active sites located in the micropores of the zeolites will be advantageous in e.g. a process like alkylation of aromatic compounds. This can be obtained by the use of mesoporous zeolites, which are characterised by possessing intracrystalline microporosity as well as intracrystalline mesoporosity.

When mesoporosity is created during the zeolite synthesis, the mesopore morphology can be controlled to a higher extent compared to methods involving post-synthesis modifications. Post-synthesis modifications are characterised by partial destruction of the zeolite framework and this can lead to partial blocking of the micropores, i.e. reduce the accessibility of the active sites located in the micropores.

It is therefore an objective of the invention to provide an alkylation process for monocyclic aromatic hydrocarbons using mesoporous catalysts having improved selectivity.

The invention concerns a process for the catalytic alkylation of monocyclic aromatic compounds in a hydrocarbon process stream comprising contacting the monocyclic aromatic compound-containing hydrocarbon process stream with an alkylation agent under alkylation conditions with a mesoporous zeotype catalyst having an intracrystalline, non-crystallographic mesopore system and a mesopore volume of the zeotype crystals above 0.25 ml/g.

The invention also concerns a composition for use in the above alkylation process comprising a monocyclic aromatic compound-containing hydrocarbon process steam, an alkylation agent and a mesoporous zeotype catalyst having an intracrystalline, non-crystallographic mesopore system and a mesopore volume of the zeotype crystals above 0.25 ml/g.

The mesoporous zeotype catalysts used in the process of the invention do not include mordenite-type zeolites.

The present invention relates to the production of alkylated monocyclic aromatic compounds by alkylation of monocyclic aromatic compounds with a suitable alkylation agent. Examples of such alkylating agents are ethene and ethanol. The preferred reaction is obtained by contacting the monocyclic aromatic compound with one of the alkylating agents in the vapour phase at conditions effective for accomplishing the alkylation process in the presence of a catalyst.

The catalyst applied in the process of the invention comprises a mesoporous zeotype component that is characterised by the features described in U.S. Patent Application No. 2001/0003117 and U.S. Patent Application No. 2002/0034471, both of which are incorporated herein by reference. Zeotypes as used herein are defined according to A. Dyer, An Introduction to Zeolite Molecular Sieves, J. Wiley and Sons, Chichester, 1988. The aforementioned U.S. patent applications disclose the preparation of large zeotype primary crystals possessing determined and tunable intracrystalline mesopore systems, tortuous or straight, respectively.

These mesoporous zeotype catalysts having the features described in the U.S. disclosures mentioned above have the advantage of showing improved selectivities when used in the process of the invention and when compared to conventional microporous and mesoporous zeolites.

These zeotypes can for example be mesoporous zeolites such as MFI-type zeolites and preferably mesoporous ZSM-5 or mesoporous HZSM-5. ZSM-5 crystals prepared according to the processes described in the above disclosures have sizes typically exceeding 0.5 micrometer in two directions as measured by transmission or scanning electron microscopy (TEM or SEM, respectively). They have an external surface area greater than 30 m$^2$/g. Although mesoporous ZSM-5 is typically synthesised as an aluminosilicate, the framework aluminium can be partially or completely replaced by other trivalent elements, such as boron, iron and/or gallium or left out completely. The framework silicon can be replaced partially by other tetravalent elements such as germanium or titanium.

The terms mesoporous and mesopore(s) used herein refer to mesoporous zeotypes containing pores within each individual crystal having a pore size range according to the IU-PAC definition of mesopores, i.e. a pore diameter in the range 2-50 nanometer. The catalyst used in the process of the invention is a solid, crystalline material with the characteristic feature of possessing an intracrystalline mesopore system as well as a micropore system, where the former is non-crystallographic and the latter is crystallographic.

The mesopore volume of the zeotypes used in the process have values above 0.25 ml/g. However, mesopore volumes above 0.35 ml/g are preferred. In a most preferred embodiment of the invention the mesopore volume is above 0.45 ml/g.

The mesoporous zeolitic material is formed by introducing a mesoporous system in the zeolite crystal. This is done by crystallising the zeolite around a removable matrix consisting of some form of carbon or similar materials, which can be removed by combustion or otherwise, after the crystallisation of the zeolite. Examples of suitable matrix materials are carbon Black Pearls, which lead to the introduction of tortuous channels in the zeolite material and carbon nanotubes leading to the introduction of straight channels in the zeolite material.

The presence of tortuous or straight channels in the zeolite material leads to an increased available surface area and easier access to the active sites in the catalyst crystals.

The mesoporous ZSM-5 crystals are useful as catalysts in hydrocarbon conversion reactions, where high activity and/or rapid diffusion of the reactants and/or products out of the zeolite catalyst micropores are important, as for example in the hydroisomerization of paraffins [J. Houzvicka, C. J. H. Jacobsen, I. Schmidt, Stud. Surf. Sci. Catal., 135 (2001) 158].

The mesoporous zeolitic material is introduced into a fixed-bed reactor either pure or as a mixture with binder material, inert material or other materials not affecting the catalytic reaction. When the acidic monofunctional, mesoporous ZSM-5 crystals are used as catalysts in the process of the invention, it may be desirable to incorporate the large mesoporous zeolite crystals together with one or more other materials resistant to the temperatures and other conditions employed in the processes for which they are used. Such materials include active or inactive, natural or synthetic, porous or non-porous materials with the zeolite content ranging from 1 to approximately 90% by weight. The obtained catalyst or catalyst precursor is introduced to a reactor either pure or as a mixture with binder material, inert material or other materials not affecting the catalytic reaction. These materials can be added in order to obtain the desired shape, heat and mass-transfer characteristics and mechanical resistance. Zeolite-based catalysts are often prepared using suitable binders and/or fillers such as alumina, silica, silica-alumina, aluminasilicates, etc.

The reaction is carried out in a fixed-bed reactor containing the catalyst and possibly additional inert material, through which a gaseous mixture of the reactants is fed at a constant or varying flow rate as determined by the weight hourly space velocity, WHSV, based on the weight of material. General reaction conditions for alkylation of the monocyclic aromatics are temperatures of 100-550° C. and pressures ranging from atmospheric pressure to 200 bars. Particularly, the conditions for alkylation of benzene with ethene require a reaction temperature between the critical temperature for benzene, 289.5° C. and 500° C., a pressure between atmospheric pressure and 30 bars, a molar ratio of benzene to ethene between 1 and 20 and a total feed, WHSV, of between 1 and 2000 h$^{-1}$.

The alkylation process can be carried out batchwise or as a continuous process in either a fixed bed or a fluidised or moving bed system. Generally, it is operated as described in U.S. Pat. No. 3,751,504, while employing mesoporous zeotype catalysts. This patent describes a secondary transalkylation reactor, where diethylated benzene is reacted with benzene in a transalkylation reaction to increase the yield of ethylbenzene.

In the process of the invention the reactants, i.e. the monocyclic aromatic compound and the alkylating agent, and the products, i.e. the alkylated monocyclic aromatic compound can all be in the gas phase. It is also possible to have at least one reactant or product in the liquid phase and at least one reactant or product in the gas phase.

Formation of polyethylbenzene (PEB) and oligomerisation of ethene leads to production of resinous compounds in the reaction zone, which can cause the formation of coke-like deposits on the active surface of the catalyst leading to a decrease in activity of the catalyst material. Appropriate temperature, pressure and space velocities must be chosen to avoid or minimise this deactivation.

The hydrocarbon process stream contains at least one monocyclic aromatic compound, which can be alkylated. Examples of mono-cyclic aromatic compounds that can undergo alkylation are, amongst others, benzene, toluene and ethyl benzene.

The alkylating agent can for instance be ethene or ethanol. The use of these alkylating agents results in the addition of an ethyl group to the mono-cyclic aromatic compound.

EXAMPLES

Examples 1-3 describe the preparation of mesoporous and reference zeolite catalysts. The reference material is a non-mesoporous zeolite in all cases. Several different techniques are employed to characterise the catalysts. All percentages are by weight unless otherwise stated.

Examples 4-6 describe the alkylation process with the alkylating agent.

Example 1

Preparation of Mesoporous ZSM-5 using Carbon Black Pearls 2.1 g of NaAlO$_2$ (29.3 w % Al) is dissolved in a mixture of 172.0 g of tetrapropylammoniumhydroxide solution (TPAOH, 40 w % in water) and 25.75 g of distilled water. 151.5 g of ethanol (EtOH, 99% pure) is added and the mixture is impregnated onto 100 g of carbon (Black Pearls, pearl diameter 18 nm), which has previously been dried at 140° C. for 24 hours. The impregnated carbon is left 24 hours at room temperature, whereupon the ethanol evaporates. 193.5 g of tetraethylorthosilicate (TEOS) is impregnated onto the carbon, which is left 24 hours at room temperature in which time the alkoxides present will hydrolyse.

The impregnated carbon is hydrothermally treated in an autoclave, which has been charged with sufficient water to create a saturated steam atmosphere at the hydrothermal crystallisation conditions. The autoclave is heated to 180° C. and held at this temperature for 72 hours. The resulting powder is filtered, washed twice with water and once with ethanol and dried at 110° C. Subsequently, the matrix is removed by heating the sample to 550° C. at 2° C./min. temperature ramping and held at this temperature for 12 hours.

The resulting white powdery product is suspended in a solution of $NH_3$ and $CH_3COONH_4$ (1:1 molar ratio) at 70° C. for 2 hours, filtered, washed, dried at 110° C. and calcined for 4 hours at 550° C. Properties of the resulting product are depicted in Table 1.

TABLE 1

| Property | Technique | Result |
| --- | --- | --- |
| Crystallinity | X-ray powder diffraction | 100% crystalline MFI structure |
| Single crystal | Transmission electron microscopy | Single crystal |
| Crystal size | Scanning electron microscopy | 2 μm |
| Acidity as Si/Al molar ratio | Ammonia desorption | 116 |
| | $^{27}$Al-NMR | 120 |
| | Infrared spectroscopy[1] | 110 |
| Pore size | $N_2$ ads./des. At 77 K, t-plot method | Micropores: ~0.5 nm radius |
| | $N_2$ ads./des. At 77 K, BJH method | Mesopores: 2–25 nm radius |
| Pore volume | $N_2$ ads./des. At 77 K, t-plot method | Micropores: 0.09 mL/g |
| | $N_2$ ads./des. At 77 K, BJH method | Mesopores: 0.50 mL/g |

[1]Probe molecule was pyridine

From the X-ray powder diffraction patterns (XRPD) obtained it is seen that the sample contains only crystalline MFI-type material. The pore size distributions obtained from the isotherms measured reveals a bimodal pore size distribution with micropores of approximately 0.5 nm radius and mesopores in the range of 2-25 nm radius. The pore volumes of the micropores and mesopores were 0.09 and 0.50 mL/g, respectively. To demonstrate that the zeolite crystals are actually single crystals rather than just agglomerates of smaller crystals, selected area electron diffraction patterns were obtained from a number of crystals and they all showed single crystal properties. Inspection of high-resolution transmission electron micrographs from these single crystals also revealed that the lattice fringes extend through the entire crystal. Transmission electron micrography (TEM) of the resulting zeolite crystals showed tortuous channels, created by matrix removal and reflecting the sizes of the carbon Black Pearls.

Example 2

Preparation of Mesoporous ZSM-5 using carbon nanotubes 2 g carbon nanotubes (CNT's, Supplied by Hyperion Catalysis International, pre-dried overnight at 130° C.) in a beaker is impregnated with 4 g of tetraethylorthosilicate (TEOS) by dropwise addition. The sample is subsequently placed in a dessicator over a 25 wt % aqueous ammonia solution for 10 hours, allowing the TEOS to hydrolyse. Then 1.35 g $H_2O$ is added and after digestion for 3 hours a premixed clear solution comprising 4.0 g 40 w % tetrapropylammonium hydroxide (TPAOH), 0.036 g sodium aluminate ($NaAlO_2$, 54 w % $Al_2O_3$, 41 w % $Na_2O$), 0.5 g $H_2O$, and 1.0 g ethanol (EtOH) is added dropwise without exceeding the porevolume. The sample is aged for 10 hours at ambient temperature. The sample is then transferred to a porcelain cup in an autoclave, which has been charged with sufficient water to create a saturated steam atmosphere at the hydrothermal crystallisation conditions. The autoclave is heated to 175° C. and held at this temperature for 72 hours. The cooled sample is washed with distilled water, filtered on a Buchner filter and dried at 110° C. Subsequently, the matrix is removed by heating the sample to 600° C. at 2° C./min. and held at this temperature for 11 hours. Properties of the resulting product are depicted in Table 2.

TABLE 2

| Property | Technique | Result |
| --- | --- | --- |
| Crystallinity | X-ray powder diffraction | 100% crystalline MFI structure |
| Single crystal | Transmission electron microscopy | Single crystal |
| Crystal size | Scanning electron microscopy | 0.5 μm |
| Acidity as Si/Al molar ratio | Ammonia desorption | 106 |
| | $^{27}$Al-NMR | 112 |
| | Infrared spectroscopy[1] | 109 |
| Pore size | $N_2$ ads./des. At 77 K, t-plot method | Micropores: ~0.5 nm radius |
| | $N_2$ ads./des. At 77 K, BJH method | Mesopores: 5–18 nm radius |
| Pore volume | $N_2$ ads./des. At 77 K, t-plot method | Micropores: 0.10 mL/g |
| | $N_2$ ads./des. At 77 K, BJH method | Mesopores: 0.40 mL/g |

[1]Probe molecule was pyridine

X-ray powder diffraction (XRPD) characterisation verified the presence of a crystalline MFI-type material. The pore size distributions obtained from the isotherms measured reveals a bimodal pore size distribution with micropores of approximately 0.5 nm radius and mesopores in the range of 5-18 nm radius. The pore volumes of the micropores and mesopores were 0.10 and 0.40 mL/g, respectively. Transmission electron micrography (TEM) of the resulting zeolite crystals showed straight channels created by matrix removal, reflecting the sizes of the carbon nanotubes.

Electron diffraction verified that the mesopores were not a result of agglomeration of small crystals, but rather intracrystalline mesopores, i.e. each of the micronsized domains are individual crystals.

Example 3

Preparation of Reference ZSM-5

0.83 g of $NaAlO_2$ (29.3 w % Al) is dissolved in a mixture of 80,0 g of tetrapropylammoniumhydroxide solution (TPAOH, 40 wt % in water) and 240 g of distilled water. 21.0 g colloidal silica (40 wt % in water) is added under stirring. The resulting gel is hydrothermally treated in an autoclave. The autoclave is heated to 180° C. and held at this temperature for 48 hours. The resulting white powder is filtered, washed twice with water and once with ethanol, dried, and calcined at 600° C. for 3 hours. The resulting white powdery product is suspended in a solution of $NH_3$ and $CH_3COONH_4$ (1:1 molar ratio) at 60° C. for 1 hour, filtered, washed, dried and calcined for 3 hours at 600° C. Properties of the resulting product are depicted in Table 3.

TABLE 3

| Property | Technique | Result |
| --- | --- | --- |
| Crystallinity | X-ray powder diffraction | 100% crystalline MFI-structure |
| Crystal size | Scanning electron microscopy | 2 μm |
| Acidity as Si/Al molar ratio | Ammonia desorption | 71 |
|  | $^{27}$Al-NMR | 70 |
|  | Infrared spectroscopy[2] | 70 |
| Pore size | $N_2$ ads./des. At 77 K, t-plot method | Micropores: ~0.5 nm radius |
|  | $N_2$ ads./des. At 77 K, BJH method | Mesopores: n.a. |
| Pore volume | $N_2$ ads./des. At 77 K, t-plot method | Micropores: 0.10 mL/g |
|  | $N_2$ ads./des. At 77 K, BJH method | Mesopores: n.a. |

[2])Probe molecule was pyridine

From the X-ray powder diffraction patterns obtained it is seen that the sample contains only crystalline MFI-type material. The pore size distributions obtained from the isotherms measured reveals a pore size distribution with micropores of approximately 0.5 nm radius. The pore volume of the micropores was 0.10 mL/g.

Example 4

Alkylation of Benzene with Ethene Using Mesoporous ZSM-5 at 370° C. with a WHSV=225 $h^{-1}$.

150 mg of the catalyst from Example 1 was mounted in a tubular fixed-bed reactor with an inner diameter of 4 mm between quartz wool plugs. The reactor was heated to 370° C. Benzene as liquid was feed into a separate vapouriser at 200° C. with a flow rate of 600 μL/min and introduced into the ethene feed, which was fed also at 200° C. and with a flow rate of 30 NmL/min. The exit gas was analysed by gas chromatography. Experiments were run at 2.5 bars and 5 bars total pressure.

TABLE 4

| Parameter | Value | |
| --- | --- | --- |
| Catalyst | 150 mg mesoporous ZSM-5 Si/Al = 120 | |
| Temperature | 370° C. | |
| Feed | | |
| Benzene | 600 μL/min | |
| Ethene | 30 NmL/min | |
| WHSV total feed | 225 $h^{-1}$ | |
| Molar ratio benzene/ethene | 5.1:1 | |
| Conversions | At 2.5 bar | At 5 bar |
| Benzene | 18% | 20% |
| Ethene | 69% | 70% |
| TOF* | At 2.5 bar | At 5 bar |
|  | 0.97 $s^{-1}$ | 1.17 $s^{-1}$ |
| Selectivities: | At 2.5 bar | At 5 bar |
| Selectivity to ethyl benzene | 81% | 75% |
| Selectivity to diethyl benzene | 19% | 25% |
| Selectivity to other products | <0.5% | <0.5% |

*Turnoverfrequency TOF defined as molar amount of benzene converted per active site per second.

Since the molar ratio of benzene to ethene is 5:1, the maximum conversion for benzene is 20% and for ethene 100%. At 370° C. the results are close to maximum conversion, the highest conversions at high pressure as expected. High selectivity to ethylbenzene and correspondingly high yields are obtained.

Example 5

Alkylation of Benzene with Ethene Using Reference ZSM-5 at 370° C. with a WHSV=225 $h^{-1}$.

150 mg of the catalyst from Example 3 was mounted in a tubular fixed-bed reactor with an inner diameter of 4 mm between quartz wool plugs. The reactor was heated to 370° C. Benzene as liquid was feed into a separate vapouriser at 200° C. with a flow rate of 600 μL/min and introduced into the ethene feed, which was fed also at 200° C. and with a flow rate of 30 NmL/min. The exit gas was analysed by gas chromatography. Experiments were run at 2.5 bar and 5 bar total pressure.

TABLE 5

| Parameter | Value | |
| --- | --- | --- |
| Catalyst | 150 mg reference ZSM-5 Si/Al = 70 | |
| Reaction conditions | 370° C. | |
| Feed | | |
| Benzene | 600 μL/min | |
| Ethene | 30 NmL/min | |
| WHSV total feed | 225 $h^{-1}$ | |
| Molar ratio benzene/ethane | 5.1:1 | |
| Conversions | At 2.5 bar | At 5 bar |
| Benzene | 15% | 20% |
| Ethene | 65% | 80% |
| TOF* | At 2.5 bar | At 5 bar |
|  | 0.47 $s^{-1}$ | 0.56 $s^{-1}$ |
| Selectivities: | At 2.5 bar | At 5 bar |
| Selectivity to ethylbenzene | 73% | 55% |
| Selectivity to diethylbenzene | 27% | 45% |
| Selectivity to other products | <1% | <1% |

*Turnoverfrequency TOF defined as molar amount of benzene converted per active site per second.

Almost total conversion is again seen at 5 bars. Comparing with Example 4 at 2.5 bars, noticeable differences can be seen: the reference material exhibits a lower conversion at 370° C. compared to the mesoporous material away from the maximum conversion, even though the reference material is more acidic. The TOF of the reference material is only half of the mesoporous material. Also a significantly lower selectivity to ethylbenzene for the reference material can be seen.

Example 6

Comparison of Mesoporous and Reference ZSM-5 Based Catalysts for Alkylation of Benzene with Ethene at 310° C. with a WHSV=225.

150 mg of the catalyst from Example 1 and in a subsequent experiment 150 mg of the catalyst from Example 3 were mounted in a tubular fixed-bed reactor with an inner diameter of 4 mm between quartz wool plugs. The reactor was heated to 310° C. The pressure was 2.5 bar. Benzene as liquid was feed into a separate vaporiser at 200° C. with a flow rate of 600 μL/min and introduced into the ethene feed, which was fed also at 200° C. and with a flow rate of 30 NmL/min. The exit gas was analysed by gas chromatography.

TABLE 6

| Parameter | Value | Value |
|---|---|---|
| Catalyst | 150 mg mesoporous ZSM-5 Si/Al = 120 | 150 mg reference ZSM-5 Si/Al = 70 |
| Reaction conditions | 310° C. | 310° C. |
| Feed | | |
| Benzene | 600 µL/min | 600 µL/min |
| Ethene | 30 NmL/min | 30 NmL/min |
| WHSV total feed | 225 h$^{-1}$ | 225 h$^{-1}$ |
| Molar ratio benzene/ethene | 5.1:1 | 5.1:1 |
| Conversions | | |
| Benzene | 4% | 4% |
| Ethene | 22% | 29% |
| TOF* | 0.22 s$^{-1}$ | 0.14 s$^{-1}$ |
| Selectivities: | | |
| Selectivity to ethylbenzene | 88% | 83% |
| Selectivity to diethylbenzene | 12% | 17% |
| Selectivity to other products | <0.5% | <0.5% |

*Turnoverfrequency TOF defined as molar amount of benzene converted per active site per second.

Comparing the results at 310° C., where the conversions are small and far from maximum conversion, the same differences as in Examples 4 and 5 are seen. The mesoporous material exhibits a higher TOF and higher selectivity to ethylbenzene.

The invention claimed is:

1. A process for the catalytic alkylation of monocyclic aromatic compounds in a hydrocarbon process stream comprising:
    applying a synthesis gel with zeolite catalyst precursor composition within the pore system and on the surface of a particulate matrix material having a predetermined pore structure and particle size;
    subjecting the catalyst precursor composition to crystallizing conditions; and
    isolating porous single crystals of mesoporous zeolite catalyst having intracrystalline, non-crystallographic mesopores and a mesopore volume of the zeolite crystals above 0.25 ml/g, by removing the matrix material; and
    contacting the monocyclic aromatic compound containing hydrocarbon process stream with an alkylation agent under alkylation conditions with the mesoporous zeolite catalyst to form an alkylated monocyclic aromatic compound.

2. The process according to claim 1, wherein the matrix material consists of carbon particles.

3. The process according to claim 1, wherein the zeolite is a mesoporous MFI-type zeolite.

4. The process according to claim 3, wherein the MFI-type zeolite is HZSM-5.

5. The process according to claim 1, wherein the monocyclic aromatic compound is benzene, toluene or ethyl benzene.

6. The process according to claim 1, wherein the alkylating agent is ethene or ethanol.

7. The process according to claim 1, wherein the catalyst comprises a binder material selected from the group consisting of alumina, silica and silica-alumina.

8. The process according to claim 1, wherein the alkylation conditions comprise a pressure between 1 bar and 30 bars.

9. The process according to claim 1, wherein the molar ratio between the monocyclic aromatic compound and the alkylation agent is between 1 and 20.

10. The process according to claim 1, wherein the mesopore volume is above 0.35 ml/g.

11. The process according to claim 10, wherein the mesopore volume is above 0.45 ml/g.

* * * * *